United States Patent [19]
Grey

[11] Patent Number: 6,037,484
[45] Date of Patent: Mar. 14, 2000

[54] EPOXIDATION PROCESS

[75] Inventor: Roger A. Grey, West Chester, Pa.

[73] Assignee: Arco Chemical Technology, L.P., Greenville, Del.

[21] Appl. No.: 09/158,396

[22] Filed: Sep. 22, 1998

[51] Int. Cl.[7] .................................................. C07D 301/12
[52] U.S. Cl. ............................................................ 549/531
[58] Field of Search ............................................. 549/531

[56] References Cited

U.S. PATENT DOCUMENTS

| | | | |
|---|---|---|---|
| 4,824,976 | 4/1989 | Clerici et al. | 549/531 |
| 4,833,260 | 5/1989 | Neri et al. | 549/531 |
| 5,591,875 | 1/1997 | Chang et al. | 549/531 |
| 5,646,314 | 7/1997 | Crocco et al. | 549/531 |
| 5,675,026 | 10/1997 | Thiele | 549/531 |

OTHER PUBLICATIONS

Bittar et al, "Lewis Acid Sites in Titanium Silicalite" Research on Chemical Intermediates, vol. 18, pp. 49–49 (1992).

*Primary Examiner*—Ba K. Trinh
*Attorney, Agent, or Firm*—William C. Long

[57] ABSTRACT

The selectivity of an olefin epoxidation process catalyzed by a titanium-containing zeolite is improved by performing the epoxidation in the presence of a non-ionic tertiary amine or tertiary amine oxide additive. For example, when hydrogen peroxide is reacted with propylene in the presence of TS-1 titanium silicalite to form propylene oxide, non-selective ring-opening reactions of the propylene oxide are suppressed when low concentrations of 2,6-lutidine or other substituted pyridines are added to the hydrogen peroxide feed.

25 Claims, No Drawings

EPOXIDATION PROCESS

FIELD OF THE INVENTION

This invention relates to methods whereby the selectivity of an olefin epoxidation reaction may be enhanced. In particular, the invention pertains to an epoxidation process wherein a titanium-containing zeolite is utilized in the presence of hydrogen peroxide and low concentrations of a tertiary amine or tertiary amine oxide such as a pyridine derivative to catalyze the formation of the epoxide corresponding to the starting olefin while minimizing the production of ring-opening products derived from the epoxide.

BACKGROUND OF THE INVENTION

It is well known that the epoxidation of olefinic compounds with hydrogen peroxide may be effectively catalyzed by certain synthetic zeolites containing titanium atoms (see, for example, U.S. Pat. No. 4,833,260). While selectivity to the desired epoxide is generally high, U.S. Pat. No. 4,824,976 proposes that the non-selective ring-opening reactions which take place when epoxidation is performed in a protic medium such as water or alcohol may be suppressed by treating the catalyst prior to the reaction or during the reaction with a suitable acid neutralizing agent. The neutralizing agent is said to neutralize acid groups on the catalyst surface which tend to promote by-product formation. Neutralization, according to the patent, may be accomplished with water soluble basic substances chosen from among strong bases such as NaOH and KOH and weak bases such as $NH_4OH$, $Na_2CO_3$, $NaHCO_3$, $Na_2HPO_4$ and analogous potassium and lithium salts including $K_2CO_3$, $Li_2CO_3$, $KHCO_3$, $LiHCO_3$, and $K_2HPO_4$, alkali and/or alkaline earth salts of carboxylic acids having from 1 to 10 carbon atoms and alkali and/or alkaline earth alcoholates having from 1 to 10 carbon atoms.

More recently, as described in U.S. Pat. Nos. 5,646,314, and 5,675,026 it has been found that the presence of certain nonbasic (i.e., neutral or acidic) salts such as lithium chloride, sodium sulfate, lithium nitrate, magnesium acetate and ammonium acetate also improves the selectivity of an epoxidation catalyzed by a titanium-containing zeolite.

In the aforementioned patents, however, all of the substances said to be effective in enhancing the yield of epoxide are ionic in character. That is, the selectivity-improving additives must be capable of dissociation into cationic and anionic species when dissolved in water. There is no teaching or suggestion that any non-ionic compounds might be capable of providing similar benefits when present in an olefin epoxidation system catalyzed by a titanium-containing zeolite.

SUMMARY OF THE INVENTION

We have now unexpectedly discovered that by carrying out a titanium silicalite-catalyzed epoxidation in the presence of low concentrations of a tertiary amine and/or tertiary amine oxide, selectivity to epoxide may be significantly improved. In many cases, no detrimental effect on the rate of hydrogen peroxide conversion is observed. This result was surprising in view of the belief in the art, as evidenced by U.S. Pat. Nos. 4,824,976 and 5,675,026, that only ionic species would effectively enhance epoxide selectivity.

This invention provides a method of epoxidizing an olefin comprising contacting said olefin with hydrogen peroxide in a reaction zone in the presence of a titanium-containing zeolite catalyst and an amount of a tertiary amine or oxide thereof effective to improve selectivity to epoxide.

DETAILED DESCRIPTION OF THE INVENTION

The hydrogen peroxide ($H_2O_2$) utilized as the oxidant in the present invention may be obtained from any suitable source, including, for example, from autoxidation of secondary alcohols using air or other source of molecular oxygen. Suitable secondary alcohols include both aliphatic alcohols such as isopropanol and cyclohexanol as well as aromatic alcohols such as alpha methyl benzyl alcohol and anthrahydroquinones (including alkyl-substituted anthrahydroquinones). The crude reaction product thereby generated may be either used directly in the epoxidation process of this invention or, if so desired, purified, fractionated, concentrated, ion exchanged, or otherwise processed prior to such use. For example, the ketone generated as an autoxidation co-product may be separated, in whole or in part, from the hydrogen peroxide by distillation (where the ketone is relatively volatile) or by extraction with water (where the ketone is substantially immiscible with or insoluble in water). When hydrogen peroxide per se is used as a reactant, it will be generally desirable to employ hydrogen peroxide concentrations of from about 1 to 20 weight percent in the liquid phase within the reaction zone. The hydrogen peroxide may alternatively be generated in situ by, for example, combining oxygen, hydrogen, a noble metal such as Pd (which can be impregnated into or otherwise supported on the titanium-containing zeolite), olefin, zeolite and -tertiary amine or oxide thereof within a reaction zone under conditions effective to accomplish contemporaneous hydrogen peroxide production and olefin epoxidation. The present invention thus may be readily adapted for use in the epoxidation processes described in JP 4-352771, JP H8-269029, JP H8-269030, WO 96/02323, WO 97/25143, DE 19600709, WO 97/31711, and WO 97/47386.

The ethylenically unsaturated substrate epoxidized in the process of this invention is preferably an organic compound having from two to ten carbon atoms and at least one ethylenically unsaturated functional group (i.e., a carbon-carbon double bond) and may be a cyclic, branched or straight chain aliphatic olefin. More than one carbon-carbon double bond may be present in the olefin; dienes, trienes, and other polyunsaturated substrates thus may be used. Methods of producing olefins are well-known in the art. For example, the olefin to be used in the process of this invention may be generated by dehydrogenation of the corresponding saturated compound.

Exemplary olefins suitable for use in the process of this invention include ethylene, propylene, the butenes, butadiene, the pentenes, isoprene, 1-hexene, 3-hexene, 1-heptene, 1-octene, diisobutylene, 1-nonene, the trimers and tetramers of propylene, cyclopentene, cyclohexene, cycloheptene, cyclooctene, cyclooctadiene, dicyclopentadiene, methylenecyclopropane, methylenecyclopentane, methylenecyclohexane, vinylcyclohexane, and vinyl cyclohexene.

Mixtures of olefins may be epoxidized and resulting mixture of epoxides either employed in mixed form or separated into the different component epoxides.

The process of this invention is especially useful for the epoxidation of $C_2$–$C_{10}$ olefins having the general structure

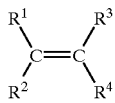

wherein $R^1$, $R^2$, $R^3$, and $R^4$ are the same or different and are selected from the group consisting of hydrogen and $C_1$–$C_8$ alkyl (selected so that the total number of carbons in the olefin does not exceed 10).

The process of this invention is also suitable for use in epoxidizing olefins containing functional groups other than aliphatic hydrocarbyl moieties. For example, the carbon-carbon double bond can be substituted with groups such as —$CO_2H$, —$CO_2R$, —CN, or —OR wherein R is an alkyl, cycloalkyl, aryl or aralkyl substituent. The radicals $R^1$, $R^2$, $R^3$, and $R^4$ in the structural formula shown hereinabove may contain aryl, aralkyl, halo, nitro, sulfonic, cyano, carbonyl (e.g., ketone, aldehyde), hydroxyl, carboxyl (e.g., ester, acid) or ether groups. Examples of such olefins include allyl alcohol, styrene, allyl chloride, allyl methyl ether, allyl phenyl ether, methyl methacrylate, acrylic acid, methyl acrylate, stilbene, and the like.

The amount of hydrogen peroxide relative to the amount of olefin is not critical, but most suitably the molar ratio of olefin: hydrogen peroxide is from about 100:1 to 1:10 when the olefin contains one ethylenically unsaturated group. The molar ratio of ethylenically unsaturated groups in the olefin to hydrogen peroxide is more preferably in the range of from 1:2 to 10:1.

The titanium-containing zeolites useful as catalysts in the epoxidation step of the process comprise the class of zeolitic substances wherein titanium atoms are substituted for a portion of the silicon atoms in the lattice framework of a molecular sieve. Such substances are well-known in the art.

Particularly preferred titanium-containing zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta, mordenite, ZSM-48, ZSM-12, and MCM-41. The titanium-containing zeolite preferably contains no elements other than titanium, silicon and oxygen in the lattice framework, although minor amounts of boron, iron, aluminum, and the like may be present. Other metals such as tin or vanadium may also be present in the lattice framework of the zeolite in addition to the titanium, as described in U.S. Pat. Nos. 5,780,654 and 5,744,619.

Preferred titanium-containing zeolite catalysts suitable for use in the process of this invention will generally have a composition corresponding to the following empirical formula $xTiO_2$: $(1-x)SiO_2$, where x is between 0.0001 and 0.500. More preferably, the value of x is from 0.01 to 0.125. The molar ratio of Si:Ti in the lattice framework of the zeolite is advantageously from 9.5:1 to 99:1 (most preferably, from 9.5:1 to 60:1). The use of relatively titanium-rich zeolites may also be desirable.

The amount of catalyst employed is not critical, but should be sufficient so as to substantially accomplish the desired epoxidation reaction in a particularly short period of time. The optimum quantity of catalyst will depend upon a number of factors including reaction temperature, olefin reactivity and concentration, hydrogen peroxide concentration, type and concentration of organic solvent as well as catalyst activity and the type of reactor or reaction system (i.e., batch vs. continuous) employed. In a batch-type or slurry reaction, for example, the amount of catalyst will typically be from 0.001 to 10 grams per mole of olefin. In a fixed or packed bed system, the optimum quantity of catalyst will be influenced by the flow rate of reactants through the fixed bed; typically, from about 0.05 to 2.0 kilograms hydrogen peroxide per kilogram catalyst per hour will be utilized. The concentration of titanium in the liquid phase reaction mixture will generally be from about 10 to 10,000 ppm.

The catalyst may be utilized in powder, pellet, microspheric, extruded, monolithic or any other suitable physical form. The use of a binder (co-gel) or support in combination with the titanium-containing zeolite may be advantageous. Supported or bound catalysts may be prepared by the methods known in the art to be effective for zeolite catalysts in general. Specific examples of supported titanium-containing zeolite catalysts suitable for use in the present process are described, for example, in U.S. Pat. Nos. 4,954,653, 5,354,875, 5,466,835, and 5,736,479. Preferably, the binder or support is essentially non-acidic and does not catalyze the non-selective decomposition of hydrogen peroxide or ring-opening of the epoxide.

Illustrative binders and supports include titania, silica, alumina, silica-alumina, silicatitania, silica-thoria, silica-magnesia, silica-zironia, silica-beryllia, and ternary compositions of silica with other refractory oxides. Also useful are clays such as montmorillonites, kaolins, bentonites, halloysites, dickites, nacrites, and ananxites. The proportion of zeolite:binder or support may range from 99:1 to 1:99, but preferably is from 5:95 to 80:20.

A critical feature of the process of this invention is the presence of a tertiary amine or tertiary amine oxide. Such additives are non-ionic in character, in contrast to the ionic species suggested by the prior art. While the precise mechanism by which the improved epoxide selectivities of the process are realized is not known, it is believed that the tertiary amine or oxide interacts in a favorable way with the titanium-containing zeolite catalyst so as to suppress undesired side reactions such as epoxide ring-opening. In one embodiment, the catalyst is pretreated (i.e., prior to epoxidation) with the tertiary amine or oxide. One suitable pretreatment method involves forming a slurry of the catalyst in a diluted solution of the tertiary amine or oxide in a suitable solvent and stirring the slurry at a temperature of from 20° C. to 100° C. for a time effective to incorporate sufficient tertiary amine or oxide into the zeolite. The catalyst is thereafter separated from the slurry by suitable means such as filtration, centrifugation, or decantation, washed if so desired (being careful not to remove all of the tertiary amine or oxide), and then, optionally, dried of residual solvent. In a preferred embodiment, however, the tertiary amine or oxide is introduced into the reaction zone separately from the catalyst during epoxidation. For example, the tertiary amine or oxide may be suitably dissolved in the hydrogen peroxide feed, which typically will also contain a relatively polar solvent such as water, alcohol, and/or ketone. In a continuous process, the concentration of tertiary amine or oxide in the feed entering the reaction zone may be periodically adjusted as desired or necessary in order to optimize the epoxidation results attained. It may, for example, be advantageous to use a constant tertiary amine or oxide concentration, to introduce portions of the tertiary amine or oxide at intermittent intervals, or to increase or decrease the tertiary amine or oxide concentration over time.

The type of tertiary amine or tertiary amine oxide preferred for use will vary somewhat depending upon the other parameters of the olefin epoxidation process which are selected, but may be readily determined by routine experimentation. In contrast to the epoxidation process described in U.S. Pat. No. 4,824,976, it is not necessary for the tertiary amine or oxide thereof to be water-soluble. Generally speaking, however, the use of an additive which is soluble in the liquid medium in which the epoxidation is performed is preferred. Without wishing to be bound by theory, it is believed that the ability of the tertiary amine or oxide to suppress the undesired ring-opening reactions of the epoxide which is formed during epoxidation is generally enhanced if the tertiary amine or oxide is sufficiently small in molecular size so as to be able to enter the pores of the titanium-containing zeolite. Thus, in the case of a relatively small-pore zeolite such as TS-1 titanium silicalite, 2,6-lutidine has been found to be much more effective than 2, 6-di-tertbutyl pyridine. At the same time, however, it will typically be desirable to have the nitrogen atom of the tertiary amine or oxide be sterically hindered to some degree in order not to decrease the epoxidation activity of the catalyst to an unacceptable degree.

In certain embodiments of the invention, the tertiary amine or oxide thereof contains a single nitrogen atom and/or is a heterocyclic compound where nitrogen is present in a cyclic structural moiety. Two or more nitrogen atoms may be present, however. Aromatic heterocycles containing nitrogen are generally suitable for use. Pyridine, substituted pyridines and oxides thereof have been found to be especially effective in reducing the levels of ring-opening side reactions which are observed during olefin epoxidation. For example, the substance to be added for such purpose may be a pyridine derivative substituted at one or both of the 2 and 6 positions of the pyridine ring with an alkyl (e.g., $C_1-C_6$) or halo group. Cyano- and alkoxy-substituted pyridines may also be used. Tertiary amines in which the nitrogen atom is attached to three carbon atoms are also generally useful in the present process.

Other classes of tertiary amines and tertiary amine oxides suitable for use include, but are not limited to:
trimethyl pyridines
2-halopyridines (chloro, bromo, iodo)
dihalopyridines (e.g., 2,6-difluoropyridine)
cyanopyridines (esp. monosubstituted compounds such a 3-cyanopyridine)
methylpyrimidines
halopyrimidines
pyrazines
1-alkyl triazoles (including halo and alkyl derivatives thereof)
triazines (including halo and alkyl derivatives thereof)
N,N-dialkyl anilines (including cyano, halo and alkyl derivatives thereof)
halo-N,N-dialkyl anilines
alkyl-N,N-dialkyl anilines
alkyl dimethyl amines (esp. where alkyl=$C_1-C_{18}$ hydrocarbon)
phenyl pyridines
2 or 4 dimethylamino pyridines (including alkyl and halo derivatives thereof)
1-alkyl imidazoles (including alkyl and halo derivatives thereof)
1-alkyl piperidines
1-alkyl morpholines and oxides thereof. Mixtures of tertiary amines and tertiary amine oxides may be utilized. Illustrative tertiary amines and oxides thereof which may be utilized in the present process include, but are not limited to, the following amines and their corresponding oxides and isomers, analogs and homologs thereof:
pyridine
2-methyl pyridine (2-picoline)
quinoxaline
quinoline
2-methyl pyrazine
3-methyl pyridine (3-picoline)
4-methyl pyridine (4-picoline)
N,N-dimethyl aniline
2,6-lutidine
2,4-lutidine
3,4-lutidine
2,6-diethyl pyridine
2,6-dipropyl pyridine
2-ethyl pyridine
2-propyl pyridine
2,3-diethyl pyrazine
2-methyl quinoline
1,2,5-trimethyl pyrrole
2-methoxypyridine
9-methyl carbazole
phenanthridine
acridine
2,2'-bipyridine
1-methyl indole
pyrimidine
2-fluoropyridine
2-chloropyridine
2-bromopyridine
2-iodopyridine
1,6-difluoropyridine
3-cyanopyridine
1-methyl triazide
1-methyl imidazole
2-dimethyl amino pyridine
1-methyl piperidine The optimum concentration of tertiary amine or oxide which is utilized will vary depending upon a number of factors, including, for example, the chemical identity of the tertiary amine or oxide, temperature, solvent, space velocity, the type of titanium-containing zeolite selected and the like, but may be readily determined by routine experimentation. Generally speaking, the level of tertiary amine or oxide in the liquid phase epoxidation reaction mixture is desirably maintained at a level sufficient to provide a tertiary amine (or oxide): Ti molar ratio in the range of from 0.5:1 to 50:1.

The epoxidation reaction temperature is preferably from 0° C. to 100° C. (more preferably from 30° C. to 80° C.), but should be selected such that selective conversion of the olefin to epoxide within a reasonably short period of time with minimal non-selective decomposition of the hydrogen peroxide is achieved. It is generally advantageous to carry out the reaction to achieve as high a hydrogen peroxide conversion as possible, preferably at least 50%, more preferably at least 90%, most preferably at least 99%, consistent with reasonable selectivities. The optimum reaction temperature will be influenced by catalyst concentration and activity, substrate reactivity, reactant concentrations, and type of solvent employed, among other factors. Reaction or residence times of from about 10 minutes to 48 hours will typically be appropriate, depending upon the above-identified variables. The reaction is preferably performed at atmospheric pressure or at elevated pressure (typically, between 1 and 100 atmospheres). Generally, it will be desirable to maintain the reaction components as a liquid mixture. For example, when an olefin such as propylene is used having a boiling point at atmospheric pressure which is less than the epoxidation temperature, a superatmospheric pressure sufficient to maintain the desired concentration of propylene in the liquid phase is preferably utilized.

The epoxidation process of this invention may be carried out in a batch, continuous, or semi-continuous manner using any appropriate type of reaction vessel or apparatus such as a fixed bed, transport bed, stirred slurry, or CSTR reactor. Known methods for conducting metal-catalyzed epoxidations using hydrogen peroxide will generally also be suitable for use. Thus, the reactants may be combined all at once or sequentially. For example, the hydrogen peroxide and/or the olefin may be added incrementally to the reaction zone.

Epoxidation may be performed in the presence of a suitable solvent in order to dissolve or disperse the reactants and to facilitate temperature control. Suitable solvents include, but are not limited to, water, alcohols (especially $C_1$–$C_{10}$ aliphatic alcohols such as methanol and isopropanol), ethers (especially aliphatic ethers such as THF and MTBE), ketones (especially $C_3$–$C_{10}$ ketones such as acetone), and mixtures of such solvents. The reaction may alternatively be carried out using two liquid phases, i.e., an organic phase and an aqueous phase. Halogenated solvents such as dichloromethane, dichloroethane and chlorohenzenes are examples of solvents suitable for use in such biphasic reaction systems.

Once the epoxidation has been carried out to the desired degree of conversion, the epoxide product may be separated and recovered from the reaction mixture using any appropriate technique such as fractional distillation, extractive distillation, liquid-liquid extraction, crystallization, or the like. After separating from the epoxidation reaction mixture by any suitable method such as filtration (as when a slurry reactor is utilized, for example), the recovered titanium-containing zeolite catalyst may be economically re-used in subsequent epoxidations. Where the catalyst is deployed in the form of a fixed bed, the epoxidation product withdrawn as a stream from the epoxidation zone will be essentially catalyst-free with the catalyst being retained within the epoxidation zone. Similarly, any unreacted olefin or hydrogen peroxide may be separated and recycled or otherwise disposed of. In certain embodiments of the instant process where the epoxide is produced on a continuous basis, it may be desirable to periodically or constantly regenerate all or a portion of the used catalyst in order to maintain optimum activity and selectivity. Suitable regeneration techniques are well-known and include, for example, calcination and solvent treatment. Regeneration can also include retreatment or reimpregnation with the tertiary amine or tertiary amine oxide.

From the foregoing description, one skilled in the art can readily ascertain the essential characteristics of this invention, and, without departing from the spirit and scope thereof, can make various changes and modifications of the invention to adapt it to various usages, conditions, and embodiments.

EXAMPLES

Example 1

A 100 mL Parr reactor equipped with a magnetic stir bar is charged with 34 grams of methanol, 200 mg. of 2,6-lutidine and 250 mg. of Ts-1 titanium silicalite containing 2.1 weight % Ti (calcined at 540–550° C. before use). After stirring for several minutes at ambient temperature, 8 grams of 30% aqueous hydrogen peroxide is added. The closed reactor is then charged with 14 grams of propylene from a Hoke pressure vessel using 400 psig of nitrogen. The reactor is heated at 40° C. for 30 minutes and cooled to 20° C. using an ice bath. The gasses from the reactor are vented into a gas bag. The reactor is pressurized to 400 psig with nitrogen and the gasses vented into another gas bag. The gas bags are analyzed by GC for oxygen, propylene oxide, propylene and $CO_2$. The volumes of the bags are measured using a wet test meter. The liquid phase is analyzed by GC for oxygenated products using acetonitrile as a standard and by LC for carboxylic acids. The hydrogen peroxide conversion is measured by reaction of an aliquot of the recovered liquid with sodium iodide and titration with sodium thiosulfate. The above reaction gave propylene oxide and propylene glycol monomethyl ether isomers in 98.5 and 0.8% selectivity, respectively. The selectivities were based on observed products on a propylene basis. The hydrogen peroxide conversion was 74%.

When the amount of 2,6-lutidine was reduced by one-half, selectivity to propylene oxide was still relatively high at 97%. Only 2.8% selectivity to propylene glycol monomethyl ethers was observed. The hydrogen peroxide conversion was 88%.

By way of comparison, when the same experiment was repeated in the absence of 2,6-lutidine only 91.6% propylene oxide selectivity was obtained. The selectivity to the undesired propylene glycol monomethyl ethers was 7.7%. A hydrogen peroxide conversion of 94% was achieved.

Example 2

The procedure of Example 1 was repeated, but using a different batch of TS-1 titanium silicalite containing 1.3 weight % Ti and a longer reaction time (2.5 hours). In the presence of 2,6-lutidine, 98% propylene oxide selectivity, 1.7% propylene glycol monomethyl ether selectivity and 0% propylene glycol selectivity were observed at a hydrogen peroxide conversion of 69%. Without the 2,6-lutidine, the propylene oxide selectivity dropped to 78% while the amount of ring-opening products rose significantly (14% selectivity to propylene glycol monomethyl ether, 4.9% selectivity to propylene glycol). Hydrogen peroxide conversion was 79%.

Example 3

The procedure of Example 2 was repeated, but using pyridine oxide instead of 2,6-lutidine. Although 94.7% propylene oxide selectivity and 4.8% propylene glycol selectivity were observed, the hydrogen peroxide conversion dropped to 25%.

Examples 4–27

The procedure of Example 1 was repeated, except for the use of a different batch of TS-1 titanium silicalite and different tertiary amines or tertiary amine oxide additives. Example 4 is a comparative example (no additive present). The results obtained are shown in Table I.

TABLE I

| Example | Additive | Mg. of Additive | PO(1) sel (%)** | PM(2) sel (%) | PG(3) sel (%) | DPM(4) sel (%) | $H_2O_2$ conv. % |
|---|---|---|---|---|---|---|---|
| 4*** | None | 0 | 86 | 12 | 1 | 0.7 | 97 |
| 5 | 2,4,6-collidine | 121 | 90 | 8.3 | 0.4 | 1 | 97 |
| 6 | 2-picoline | 100 | 99.7 | 0 | 0 | 0 | 12 |
| 7 | 2-picoline | 20 | 99.5 | 0.24 | 0 | 0 | 16 |
| 8 | 2-fluoro-pyridine | 121 | 94.5 | 5.3 | 0 | 0 | 81 |
| 9 | N,N-dimethyl aniline | 144 | 99.5 | 0.4 | 0 | 0 | 53 |
| 10 | trimethyl amine oxide | 75 | 99.7 | 0 | 0 | 0 | 12 |
| 11 | 1-methyl imidazole | 89 | 99.3 | 0 | 0 | 0 | 15 |
| 12 | 2,4-lutidine | 108 | 99 | 0 | 0 | 0 | 11 |
| 13 | 2-methoxy-pyridine | 108 | 99 | 0.8 | 0 | 0 | 78 |
| 14 | 3-cyano-pyridine | 108 | 98.3 | 1.6 | 0 | 0 | 74 |
| 15 | 2,6,ditertbutyl-pyridine | 190 | 89.5 | 8.5 | 0.8 | 1.1 | 97 |
| 16 | quinuclidine | 100 | 86.4 | 7.5 | 3.0 | 0.8 | 93 |
| 17 | 2-picoline oxide | 108 | 98.3 | 1.5 | 0 | 0 | 73 |
| 18 | pyridine | 80 | 99.6 | 0 | 0 | 0 | 19 |
| 19 | 2-dimethylamino-pyridine | 122 | 99.75 | 0 | 0 | 0 | 15 |
| 20 | 4-dimethylamino-benzonitrile | 146 | 95.3 | 3.95 | 0.54 | 0 | 94 |
| 21 | 2-cyanopyridine | 112 | 90.3 | 6.94 | 0.13 | 0.13 | 91 |
| 22 | 2-bromopyridine | 158 | 94.8 | 3.7 | 0.6 | 0.6 | 97 |
| 23 | 2-chloropyridine | 118 | 95.6 | 0.4 | 0.05 | 0.04 | 88 |
| 24 | 2,6-difluoropyridine | 121 | 89.3 | 7.62 | 1.26 | 1.28 | 89 |
| 25 | 2,6-dichloropyridine | 148 | 87.9 | 8.71 | 1.45 | 1.55 | 94 |
| 26 | 1-methylimidazole | 20 | 99.5 | 0 | 0 | 0 | 17 |
| 27 | quinoline | 131 | 98 | 1.1 | 0.2 | 0.01 | 72 |

(1)PO = propylene oxide, (2)PM = propylene glycol monomethyl ethers, (3)PG = propylene glycol
(4)DPM = dipropylene glycol monomethyl ethers
**selectivity based on observed products on a propylene basis
***comparative example

I claim:

1. A method for epoxidizing an olefin comprising contacting said olefin with hydrogen peroxide in a reaction zone in the presence of a titanium-containing zeolite catalyst and an amount of an additive selected from tertiary amines and oxides thereof effective to improve selectivity to epoxide.

2. The method of claim 1 wherein the additive is selected from the group consisting of 2,6-lutidine, 2-picoline, 2-fluoropyridine, N,N-dimethylaniline, 2-methoxypyridine, 3-cyanopyridine, 4-dimethylamino benzonitrile, 2-halopyridines, quinoline and oxides thereof.

3. The method of claim 1 wherein the additive is an aromatic heterocycle containing nitrogen.

4. The method of claim 1 wherein the additive is selected from the group consisting of pyridine, halo-, cyano-, alkoxy-, dialkylamino- and alkyl- substituted pyridines, N,N-dialkyl anilines and oxides thereof.

5. The method of claim 1 wherein the additive is a pyridine derivative substituted at one or both of the 2 and 6 positions of the pyridine ring with an alkyl group.

6. The method of claim 1 wherein said contacting is performed at a temperature of from 0° C. to 100° C.

7. The method of claim 1 wherein said reacting is performed in a liquid phase.

8. The method of claim 7 wherein the liquid phase is comprised of a solvent selected from the group consisting of water, $C_1$–$C_{10}$ alcohols, $C_3$–$C_{10}$ ketones, aliphatic ethers and mixtures thereof.

9. The method of claim 7 wherein the liquid phase comprises methanol solvent.

10. The method of claim 1 wherein the titanium-containing zeolite catalyst has an MFI, MEL or zeolite beta topology.

11. The method of claim 1 wherein the titanium-containing zeolite is TS-1 titanium silicalite.

12. The method of claim 1 wherein the olefin is a $C_2$–$C_{10}$ aliphatic olefin.

13. The method of claim 1 wherein the olefin is propylene.

14. The method of claim 1 wherein the titanium-containing catalyst has a composition corresponding to the chemical formula $xTiO_2:(1-x)SiO_2$ wherein x is from 0.01 to 0.125.

15. The method of claim 1 wherein the amount of additive is sufficient to provide an additive:titanium molar ratio in the range of from 0.5:1 to 50:1.

16. The method of claim 1 wherein the hydrogen peroxide is generated in situ.

17. A method for epoxidizing a $C_2$–$C_{10}$ aliphatic olefin comprising contacting said $C_2$–$C_{10}$ aliphatic olefin with hydrogen peroxide in a liquid phase within a reaction zone in the presence of a solvent, a titanium-containing zeolite catalyst having an MFI, MEL or zeolite beta topology, and an additive selected from the group consisting of pyridine, halo-, cyano-, alkoxy-, dialkylamino- and alkyl substituted pyridines, N,N-dialkyl anilines and oxides thereof, said additive being present at a concentration effective to provide an additive: titanium molar ratio in the range of from 0.5:1 to 50:1.

18. The method of claim 17 wherein the additive is a pyridine derivative substituted at one or both of the 2 and 6 portions of the pyridine ring with an alkyl group.

19. The method of claim 17 wherein the additive is selected from the group consisting of 2,6-lutidine, 2-picoline, 2-fluoropyridine, N,N-dimethylaniline, 2-methoxypyridine, 3-cyanopyridine, 2-halopyridines, and oxides thereof.

20. The method of claim 17 wherein the $C_2$–$C_{10}$ aliphatic olefin is propylene.

21. The method of claim 17 wherein the titanium-containing zeolite catalyst is deployed in the form of a fixed bed within the reaction zone and the $C_2$–$C_{10}$ aliphatic olefin, hydrogen peroxide, solvent, and additive are introduced into the reaction zone and a product stream comprised of an epoxide corresponding to the $C_2$–$C_{10}$ aliphatic olefin is withdrawn from the reaction zone.

22. The method of claim 17 wherein the hydrogen peroxide is generated in situ.

23. The method of claim 17 wherein the solvent is selected from the group consisting of water, $C_1$–$C_{10}$ alcohols, $C_3$–$C_{10}$ ketones, aliphatic ethers and mixtures thereof.

24. The method of claim 17 wherein the titanium-containing zeolite is TS-1 titanium silicalite.

25. The method of claim 17 wherein the solvent is methanol.

* * * * *